United States Patent

Knevels et al.

[11] Patent Number: 5,979,253
[45] Date of Patent: Nov. 9, 1999

[54] SAMPLING DEVICE FOR MOLTEN METALS

[75] Inventors: Johan Knevels, Bree; Frank Mingneau, Zonhoven, both of Belgium

[73] Assignee: Heraeus Electro-Nite International N.V., Houthalen, Belgium

[21] Appl. No.: 09/120,632

[22] Filed: Jul. 22, 1998

[30] Foreign Application Priority Data

Jul. 24, 1997 [DE] Germany ............ 197 31 830

[51] Int. Cl.$^6$ .................................................. G01N 1/12
[52] U.S. Cl. ...................................................... 73/864.58
[58] Field of Search ............... 73/DIG. 9, 864.53–864.61

[56] References Cited

U.S. PATENT DOCUMENTS

| | | |
|---|---|---|
| 3,583,236 | 6/1971 | Taylor et al. . |
| 3,824,837 | 7/1974 | Nagaoka et al. . |
| 4,037,478 | 7/1977 | Cure . |
| 4,487,082 | 12/1984 | Boron . |
| 4,535,640 | 8/1985 | Falk . |
| 4,557,152 | 12/1985 | Plessers et al. ............ 73/DIG. 9 |
| 4,699,014 | 10/1987 | Boron . |
| 4,842,418 | 6/1989 | Conti ............................ 73/DIG. 9 |
| 5,033,320 | 7/1991 | Baerts ........................... 73/DIG. 9 |

FOREIGN PATENT DOCUMENTS

| | | |
|---|---|---|
| 0 107 219 A1 | 5/1984 | European Pat. Off. . |
| 3402818 A1 | 8/1985 | Germany . |
| 7-120455 | 5/1995 | Japan . |
| 9-021795 | 1/1997 | Japan . |

*Primary Examiner*—Robert Raevis
*Attorney, Agent, or Firm*—Panitch Schwarze Jacobs & Nadel, P.C.

[57] ABSTRACT

A sampling device for molten metals, especially for molten cast iron or pig iron, has a sampling chamber arranged in a refractory body mounted on a carrier. The sampling chamber is bounded on two opposing walls by one metal plate each, and has at least one inlet opening for molten metal on a further wall. In order to create a sampling device with which samples are obtained which have the best possible white solidification and at the same time have the sturdiness necessary for an automatic sample analysis, a metal disk is separably arranged in the interior of the sampling chamber on at least one of the two metal plates. The diameter of metal disk is smaller than the diameter of the sampling chamber, and the thickness of the disk is less than the thickness of the sampling chamber.

9 Claims, 6 Drawing Sheets

SAMPLING DEVICE FOR MOLTEN METALS

BACKGROUND OF THE INVENTION

The invention concerns a sampling device for molten metals, especially for molten cast iron or pig iron, with a sampling chamber arranged in a refractory body held on a carrier which is bounded on two opposing walls by one metal chilling disk (metal plate) each, and which has at least one inlet opening for molten metals on a further wall.

Such sampling devices are known from EP 0 107 219 A1, for example. These sampling devices are suited for taking samples, especially of molten steel. The samples obtained therewith are disk-shaped and usually at least 4 mm thick. The metal plates serve to cool the samples rapidly, among other things. A similar arrangement is known from DE 34 02 818 A1. Here, plate-shaped chilling elements are set at a distance from the wall of the sampling chamber of a sampling device and mounted on the wall by means of fastening elements (screws). U.S. Pat. No. 3,824,837 discloses a measuring chamber for recording the solidus or liquidus curve, in which chilling elements are arranged which dissolve in the incoming molten metals.

For example, with molten cast iron, which has a relatively high carbon content, the so-called "white solidification" is desirable for a reliable analysis, for example for spectral analysis, since during the white solidification, the carbon bound in the melt is not precipitated during the hardening. In order to obtain the most ideal white hardening possible, a rapid sample chilling is necessary, that is, the sample itself must be as thin as possible. In modern steel factories samples are analyzed automatically. In this connection, the samples are picked up by robotic graspers and transported. These graspers pick up the disk-shaped samples on their narrow sides. The force of the grasper thereby exerted on the samples can however deform samples which are too thin. There thus exists in practice a contradiction between the smallest possible sample thickness for an ideal white solidification, on the one hand, and the need for a minimal stability of the sample necessary for the sample processing, on the other hand. Sampling devices of the prior art always generate samples whose thickness represents a compromise between the two requirements existing for the analysis of cast iron samples.

SUMMARY OF THE INVENTION

An object of the present invention, proceeding from the above-described prior art, is to create a sampling device with which samples are obtained which have the best possible white hardening, but at the same time have the sturdiness necessary for an automated sample analysis.

This object is accomplished for the sampling device described at the outset, in that in the interior of the sampling chamber on at least one of the two metal chilling disks (metal plates), a further metal disk is separably arranged, whose diameter is smaller than the diameter of the sampling chamber and whose thickness is less than the thickness of the sampling chamber. It is especially expedient for the metal disk to be arranged concentrically in a circular sampling chamber.

The metal samples obtained in such a sampling chamber have a thickness at the edge which corresponds to the thickness of the sampling chamber, and in the part to be analyzed a thickness which corresponds to the difference between the thickness of the sampling chamber and the thickness of the metal disk. This difference can almost be kept as small as desired, so that a very good white solidification can take place in the portion of the sample to be analyzed. At the same time, the sample is thick enough at its edges to possess the stability necessary for automatic processing. The metal disk practically forms a component part of the sample after removing the sample from the sampling chamber, and in addition improves stability during automatic handling. Before sample analysis, the sample can be severed in its thin area, whereby the metal disk is removed.

It is expedient that the walls of the sampling chamber not bounded by metal cooling plates during sampling have a gas permeable structure, in order to make it possible for gases present in the sampling chamber to leave the sampling chamber while the molten metal flows in, so that gas inclusions in the sample are prevented.

It is advantageous for a simple construction that a metal disk be arranged on exactly one of the chilling disks bounding the sampling chamber. Furthermore, it is expedient that the metal disk be made of copper, iron or steel.

It has furthermore proven advantageous for the thickness of the metal disk to be about 3–5 mm less than the thickness of the sampling chamber. Nonetheless, other thickness proportions are also quite conceivable.

The metal disk appropriately has a slope on its edge facing the interior of the sampling chamber. This slope prevents the formation of eddies when the molten metals flow into the sampling chamber, so that air inclusions are avoided and the sampling chamber is completely filled. The slope lies opposite the inlet opening. It can run around the entire edge facing the interior of the sampling chamber. Instead of a slope, which is also frequently designated as a chamfer, the edge of the metal disk can also have a rounding, that is, be rounded off.

It can also prove to be advantageous for the metal disk to have on its edge bordering on the wall of the sample chamber an undercut which, for example, can likewise be constructed as a slope or a rounding. Such an undercut leads to the sample formed in the sampling chamber partially surrounding the metal disk and guaranteeing its firm support within the sample.

Within the body a further sampling chamber can be arranged which is, for example, constructed bar-shaped, and which serves for taking a pin sample. It is thereby possible to take two samples at the same time for different analyses.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings.

DETAILED DESCRIPTION OF THE INVENTION

Figure 1:
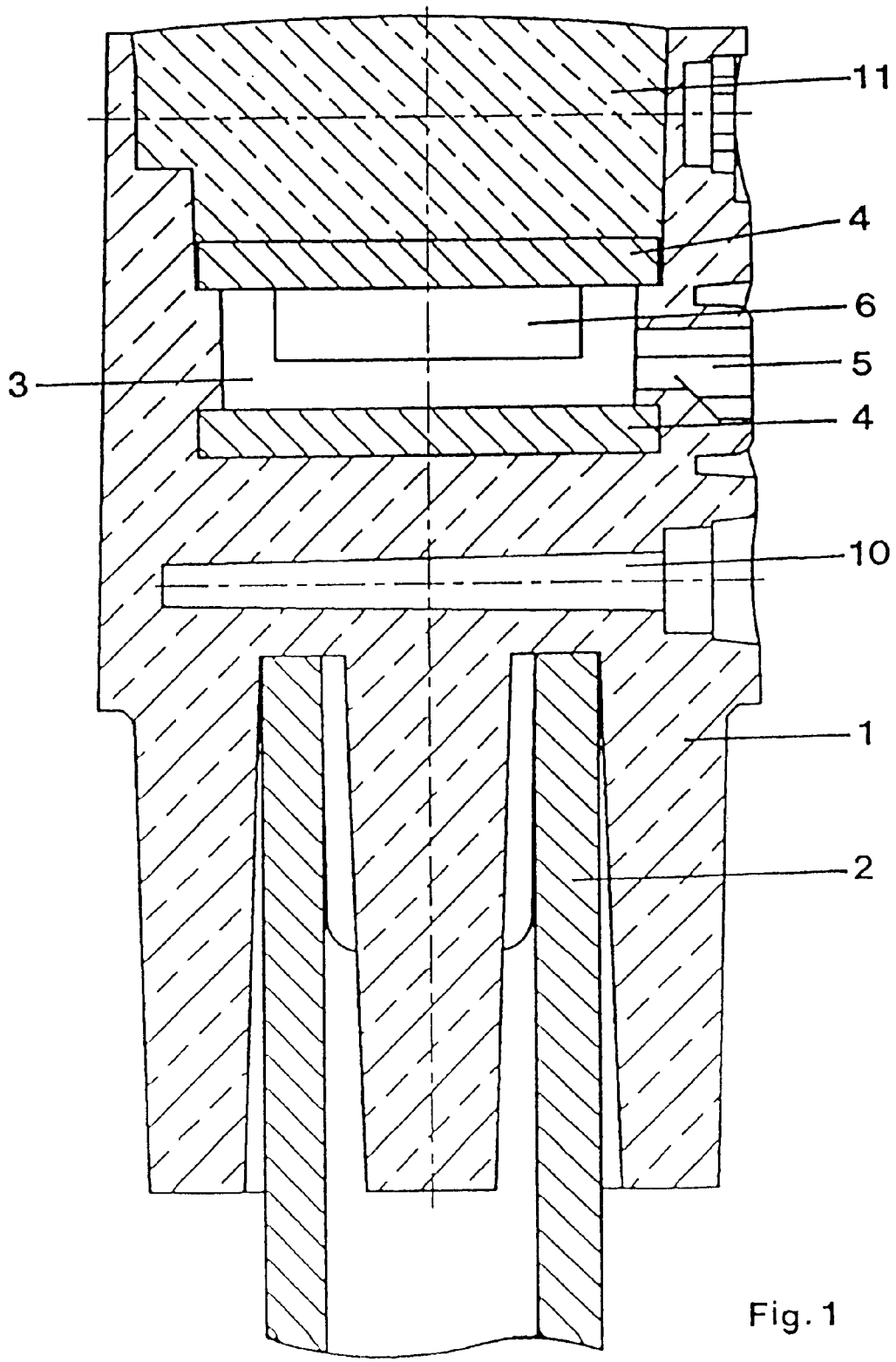
FIG. 1 depicts a sampling device in cross section.

The sampling device has refractory body 1, which is mounted on a cardboard tube 2. The refractory body 1 can either be stuck into the end of the cardboard tube 2 or onto this cardboard tube 2, so that the refractory body 1 surrounds the cardboard tube 2 on its exterior. A disk-shaped sampling chamber 3 is arranged in the refractory body 1 transverse to the longitudinal axis of the cardboard tube 2. The sampling chamber 3 has a circular cross section. Its two flat walls lying opposite one another are formed by metal chilling disks 4. The narrow side of the sampling chamber 3, a cylinder jacket surface, is made of the gas-permeable material of the refractory body 1. This material is, for example, foundry sand. Other suitable materials are also known. An inflow opening 5 opens into the narrow side of the sampling chamber 3.

A metal disk 6 of copper or iron is separably arranged, for example glued (FIG. 1), on one of the two metal chilling disks 4. The sampling chamber 3 formed thereby in practice frequently has a diameter of 35 mm and an overall thickness of about 8 mm. Other dimensions are also possible, however. The metal disk 6 has a thickness of about 4 mm, so that the portion of the sample to be analyzed likewise has a thickness of about 4 mm. Such a sample thickness is very well suited for attaining a good white solidification. The metal disk 6 has a diameter of about 25 mm in the embodiment represented.

In taking samples, the sampling device is dipped into the molten metal. The molten metal running into the sampling chamber 3, owing to the ferrostatic pressure, fills up the dish-like space. The glue is destroyed, so that the sample is removed from the sampling chamber 3 with the metal disk 6. In removing the sample from the sampling device, the metal disk 6 at first remains within the hollow space formed by the dish-like shape of the sample. An automatic grasper, which picks up the sample for processing, can reliably pick up this massive element of sample and metal disk 6 without the sample being deformed. The analysis surface of the sample (opposite the metal disk 6) forms a flat surface which is needed for analysis.

Basically, it is also conceivable that the metal disk 6 at least in part touch the edge of the sampling chamber 3, and thus form at least partially an edge area of the unit comprising the sample and the metal disk 6.

In the body 1, an additional sampling chamber 10 is arranged for taking a pin sample.

For assembling the sampling device, one of the metal cooling disks 4 (preferably the one on which the metal disk 6 is glued) is inserted into an appropriate opening of the body 1 from the immersion side of the sampling device, which opening is afterward closed with a refractory stopper 11. A very simple assembly is thereby possible.

Figure 2:
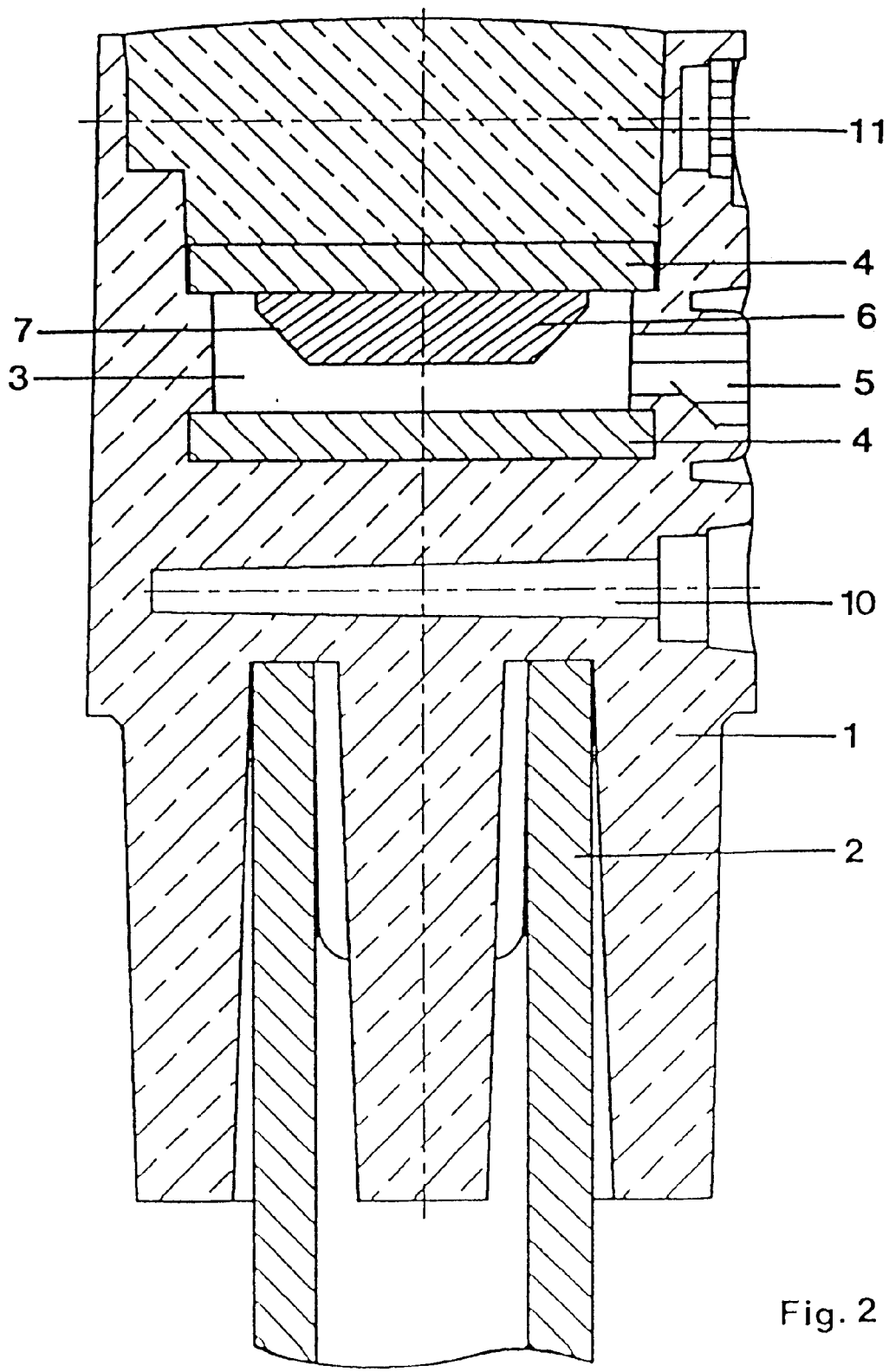
FIG. 2 illustrates a sampling device with sloped metal disk.
Figure 3:
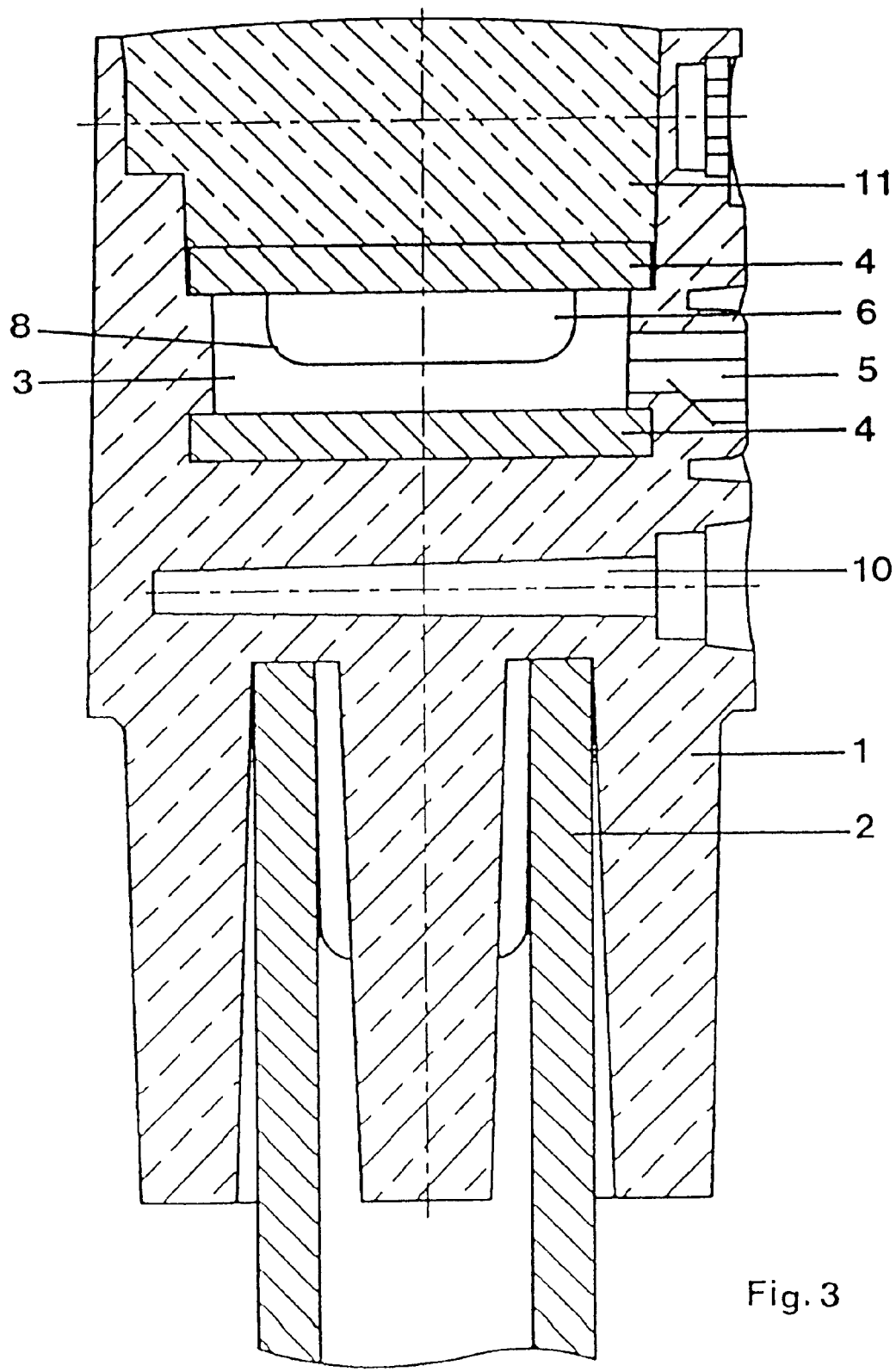
FIG. 3 shows a sampling device with rounded off metal disk.
Figure 4:
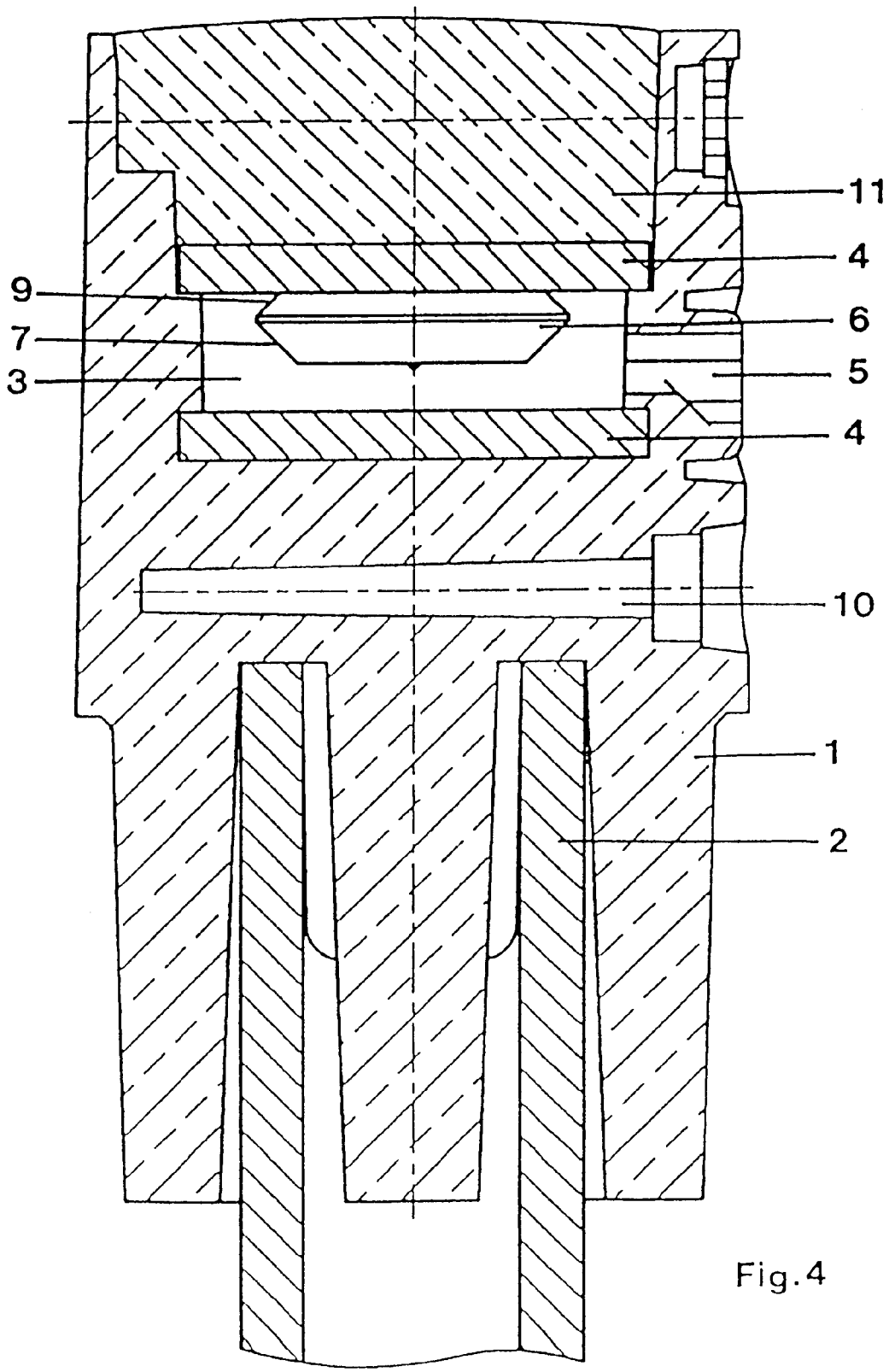
FIG. 4 illustrates a sampling device with undercut metal disk.
Figure 5:
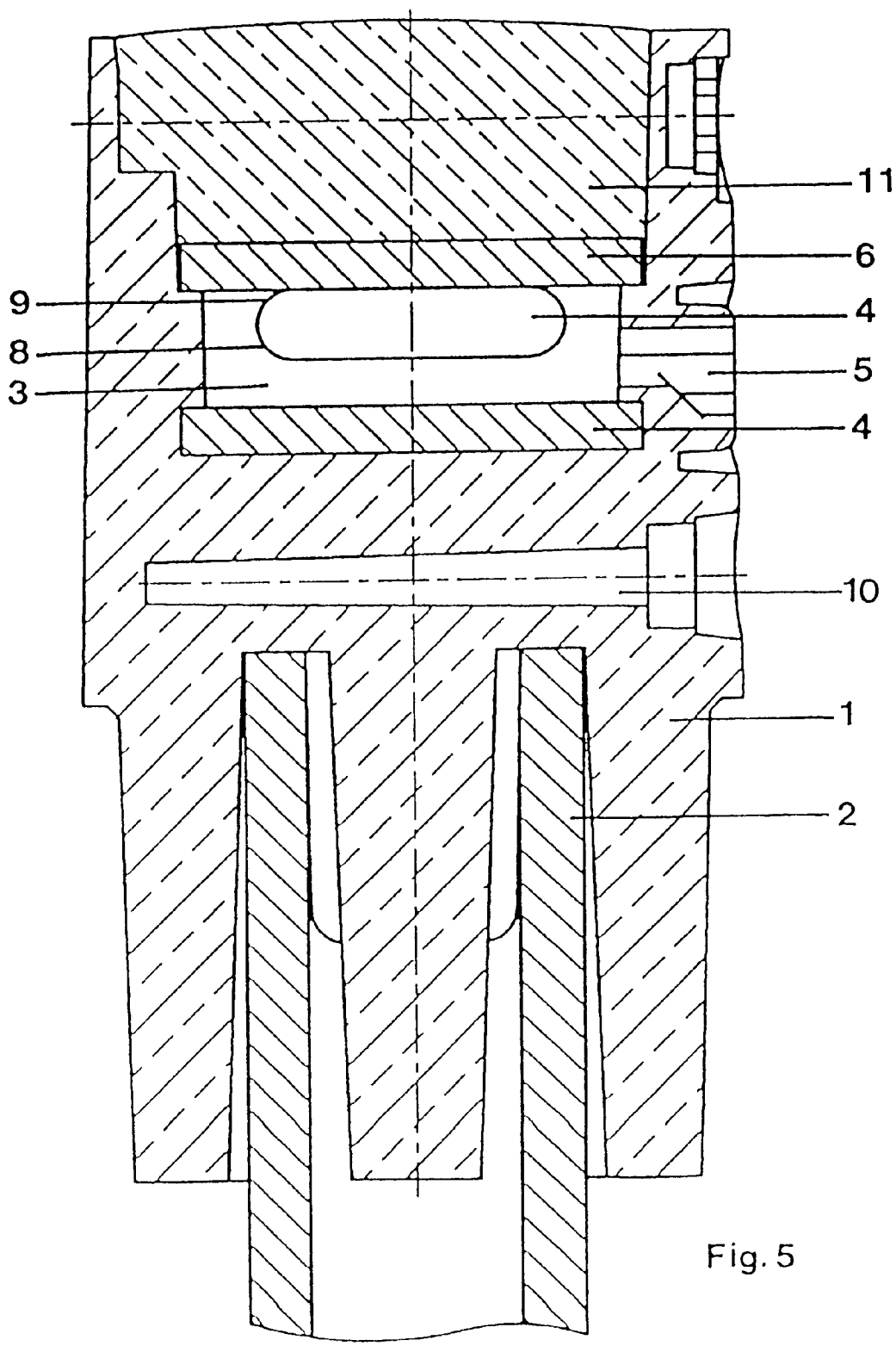
FIG. 5 depicts a further sampling device with undercut metal disk.

In FIGS. 2 to 5 particular embodiments of the sampling device are represented as examples. The individual sampling devices differ as to construction of the metal disk 6. In FIG. 2 such a metal disk 6 is represented which has a slope 7 (also called chamfer). The slope 7 serves to diminish or eliminate turbulence within the inflowing molten metal and thereby to prevent gas bubbles within the sample. A rounding 8 (FIG. 3) can be applied to metal disk 6, instead of a slope 7.

An especially firm attachment of the metal disk 6 inside the sample removed from the sampling chamber 3 arises when the metal disk 6 has an undercut 9 on its side lying against the metal chilling disk 4. It is thereby impossible for the metal disk 6 to become separated from the sample during the transport or the analysis of the sample. The undercuts represented in FIGS. 4 and 5 only serve as examples. A stepped construction or other undercuts 9 are also possible. Likewise, further combinations are also conceivable besides the combinations with a slope 7 or a rounding 8 represented in the figures.

Figure 6:
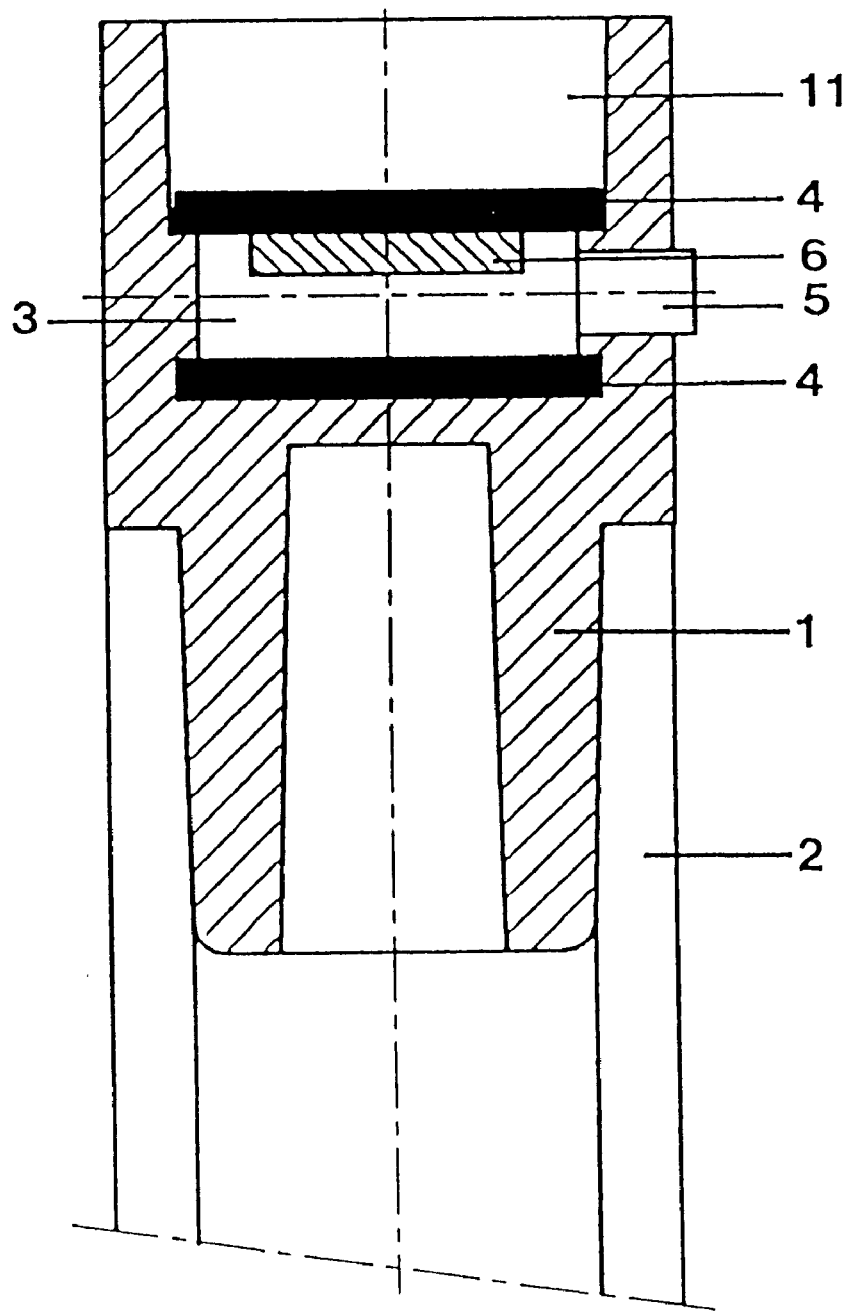
FIG. 6 shows a further embodiment of a sampling device.

A sampling device with a different type of mounting is represented in FIG. 6. For this, the refractory body 1 is partially inserted into the cardboard tube 2. The refractory body 1 has only one disk-shaped sampling chamber 3. It is, however, also possible to install a second sampling chamber 3, 10 in the refractory body 1 in connection with the mounting depicted in FIG. 6. It is likewise possible to construct sampling devices with the mounting of the cardboard tube 2 depicted in FIGS. 1 to 5 with only one sampling chamber and without the additional sampling chamber 10 (or a sampling chamber of a different type).

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

We claim:

1. A sampling device for molten metals, especially for molten cast iron or pig iron, comprising a sampling chamber (3) arranged in a refractory body (1) mounted on a carrier (2), the sampling chamber (3) being bounded on two of its opposing walls by one metal chilling disk (4) each and having at least one inlet opening (5) for molten metal on a further of its walls, and further comprising in an interior of the sampling chamber (3) a metal disk (6) separably installed on at least one of the two metal chilling disks (4), a diameter of the metal disk (6) being smaller than a diameter of the sampling chamber (3), and a thickness of the metal disk (6) being smaller than a thickness of the sampling chamber (3).

2. The sampling device according to claim 1, wherein the metal disk (6) is concentrically arranged in a circular sampling chamber (3).

3. The sampling device according to claim 1, wherein walls of the sampling chamber (3) not bounded by metal chilling disks (4) have a gas permeable structure during sampling.

4. The sampling device according to claim 1, wherein the metal disk (6) comprises copper, iron or steel.

5. The sampling device according to claim 1, wherein the thickness of the metal disk (6) is about 3–5 mm less than the thickness of the sampling chamber (3).

6. The sampling device according to claim 1, wherein the metal disk (6) has a slope (7) on its edge facing the interior of the sampling chamber (3).

7. The sampling device according to claim 1, wherein the metal disk (6) has a rounding (8) on its edge facing the interior of the sampling chamber (3).

8. The sampling device according to claim 1, wherein the metal disk (6) has an undercut (9) on its edge bordering on a the wall of the sampling chamber (3).

9. The sampling device according to claim 1, wherein the body (1) has an additional sampling chamber (10).

* * * * *